United States Patent
Watanabe (10) Patent No.: US 9,956,431 B2
(45) Date of Patent: May 1, 2018

(54) ULTRASONIC OSCILLATOR

(71) Applicant: MURAKUMO CORPORATION, Tokyo (JP)

(72) Inventor: Takahiro Watanabe, Tokyo (JP)

(73) Assignee: MURAKUMO CORPORATION, Tokyo (JP)

( * ) Notice: Subject to any disclaimer, the term of this patent is extended or adjusted under 35 U.S.C. 154(b) by 0 days. days.

(21) Appl. No.: 15/161,699

(22) Filed: May 23, 2016

(65) Prior Publication Data

US 2016/0263405 A1 Sep. 15, 2016

Related U.S. Application Data (63) Continuation of application No. PCT/JP2015/056750, filed on Mar. 6, 2015.

(51) Int. Cl.
*A61N 7/02* (2006.01)
*A61N 7/00* (2006.01)

(52) U.S. Cl.
CPC ........ *A61N 7/02* (2013.01); *A61N 2007/0052* (2013.01); *A61N 2007/0065* (2013.01); *A61N 2007/0091* (2013.01); *A61N 2007/0095* (2013.01)

(58) Field of Classification Search
CPC .............. A61N 7/02; A61N 2007/0052; A61N 2007/0065; A61N 2007/0091; A61N 2007/0095
See application file for complete search history.

(56) References Cited

U.S. PATENT DOCUMENTS

| | | |
|---|---|---|
| 4,194,510 A * | 3/1980 | Proudian .............. A61B 8/4281 600/445 |
| 4,957,099 A | 9/1990 | Hassler |
| 5,015,929 A | 5/1991 | Cathignol et al. |
| 5,624,382 A | 4/1997 | Oppelt et al. |

(Continued)

FOREIGN PATENT DOCUMENTS

| JP | 1-111476 A | 4/1989 |
|---|---|---|
| JP | 2-28212 U | 2/1990 |

(Continued)

OTHER PUBLICATIONS

Lu et al., "Mechanics of Tunable Hemispherical Electronic Eye Camera Systems That Combine Rigid Device Elements With Soft Elastomers". Journal of Applied Mechanics. Nov. 2013, Vil. 80 061022-1-061022-7.*

(Continued)

*Primary Examiner* — Long V Le
*Assistant Examiner* — Colin T Sakamoto
(74) *Attorney, Agent, or Firm* — Westerman, Hattori, Daniels & Adrian, LLP (57) ABSTRACT

Disclosed is an ultrasonic oscillator that heats a target using ultrasonic waves. The ultrasonic oscillator includes: a plurality of ultrasonic oscillation elements that oscillates the ultrasonic waves; a retention portion that retains the plurality of ultrasonic oscillation elements in a state where the ultrasonic oscillation elements are arranged along a concave thereof opposing the heating target; and a controller that controls the ultrasonic oscillation elements so as to oscillate the ultrasonic waves.

13 Claims, 3 Drawing Sheets

(56) References Cited

U.S. PATENT DOCUMENTS

| | | | |
|---|---|---|---|
| 5,713,356 A * | 2/1998 | Kruger | A61B 5/0091 |
| | | | 600/407 |
| 5,941,838 A | 8/1999 | Eizenhofer | |
| 6,027,449 A * | 2/2000 | Mazess | A61B 8/0875 |
| | | | 600/449 |
| 6,533,738 B1 | 3/2003 | Bauer et al. | |
| 6,599,256 B1 | 7/2003 | Acker et al. | |
| 6,613,005 B1 * | 9/2003 | Friedman | A61N 7/02 |
| | | | 600/371 |
| 6,719,694 B2 * | 4/2004 | Weng | A61B 17/0057 |
| | | | 310/336 |
| 8,287,471 B2 * | 10/2012 | Liu | A61N 7/02 |
| | | | 600/407 |
| 2001/0031922 A1 | 10/2001 | Weng et al. | |
| 2002/0188198 A1 * | 12/2002 | Hong | A61B 8/0825 |
| | | | 600/437 |
| 2009/0069667 A1 | 3/2009 | Lindstrom et al. | |
| 2015/0112197 A1 * | 4/2015 | Bharat | A61N 5/1049 |
| | | | 600/438 |

FOREIGN PATENT DOCUMENTS

| | | |
|---|---|---|
| JP | 2-114953 A | 4/1990 |
| JP | 6-105851 A | 4/1994 |
| JP | 7-504339 A | 5/1995 |
| JP | 8-131454 A | 5/1996 |
| JP | 2001-61854 A | 3/2001 |
| JP | 2003-517856 A | 6/2003 |
| JP | 2009-533162 A | 9/2009 |
| WO | 2004/066856 A1 | 8/2004 |

OTHER PUBLICATIONS

Abouiroux et al., "An MR-compliant phased-array HIFU transducer with augmented steering range, dedicated to abdominal thermotherapy". Physics in Medicine and Biology. 56 (2011) 3563-3582.*

Deng et al., "A multi-frequency sparse hemispherical ultrasound phased array for microbubble-mediated transcranial therapy and simultaneous cavitation mapping". Physics in Medicine and Biology. 61 (2016) 8476-8501.*

Malietzis et al., "High-intensity focused ultrasound: advances in technology and experimental trials support enhanced utility of focused ultrasound surgery in oncology" British Journal of Radiology. vol. 86 issue 1024.*

International Search Report dated Jun. 2, 2015, issued in counterpart International Application No. PCT/JP2015/056750 (3 pages).

Notification of Reason for Refusal dated Nov. 4, 2015, issued in counterpart of JP 2015-541723, with English translation (9 pages).

Extended (supplementary) European Search Report dated Oct. 24, 2017, issued in counterpart European Application No. 15859997.7. (8 pages).

* cited by examiner

ULTRASONIC OSCILLATOR

CROSS-REFERENCE TO RELATED APPLICATION

This application is a continuation application of International Application PCT/JP2015/056750 filed on Mar. 6, 2015 and designated the U.S., the entire contents of which are incorporated herein by reference.

FIELD

The present invention relates to an ultrasonic oscillator.

BACKGROUND

In the prior art, there has been proposed an ultrasonic probe including: an oscillator for treatment that has a plurality of arrayed first oscillation elements and applies ultrasonic waves for treatment to a subject; and an oscillator for diagnosis that has a plurality of arrayed second oscillation elements and applies ultrasonic waves for diagnosis to the subject and receives the ultrasonic waves for diagnosis reflected by the subject, in which the oscillator for treatment and the oscillator for diagnosis are stacked on top of one another (see WO 2004/066856).

In addition, there has been proposed an ultrasonic treatment device including: an ultrasonic generation source that generates ultrasonic waves for treatment; and drive means that drives the ultrasonic generation source such that the frequencies of the ultrasonic waves for treatment generated from the ultrasonic generation source change with time (see Japanese Patent Application Laid-open No. H8-131454).

In the prior art, there have been proposed devices that oscillate ultrasonic waves to heat targets. For the conventional devices, however, users are required to mechanically control the positions of ultrasonic oscillation elements with high accuracy so as to adjust correctly the positions that are heated using ultrasonic waves, and thus the burden that falls on the users operating such devices is heavy. Further, when such heating is used for treatment, persons to be treated are also forced to bear heavy burdens due to the considerable time required for preparations before the heating, severe limitations on the persons' body movement during the treatment, and so on.

In view of the above problems, the present invention has an object of correctly heating a target with simpler device configuration and user operations than in the prior art.

SUMMARY

The present invention employs the following means for achieving the above object. That is, an example of the present disclosure provides an ultrasonic oscillator that heats a target using ultrasonic waves, the ultrasonic oscillator including: a plurality of ultrasonic oscillation elements that oscillates the ultrasonic waves; a retention portion that retains the plurality of ultrasonic oscillation elements in a state where the ultrasonic oscillation elements are arranged along a concave thereof opposing the heating target; and a controller that controls the ultrasonic oscillation elements so as to oscillate the ultrasonic waves.

According to the present invention, it is possible to correctly heat a target with simpler device configuration and user operations than in the prior art.

DESCRIPTION OF EMBODIMENTS

Hereinafter, a description will be given of an embodiment of an ultrasonic oscillator according to the present disclosure based on the drawings. However, the following embodiment is only for illustration purpose and does not limit the ultrasonic oscillator according to the present disclosure to the following specific configuration. For the implementation of the ultrasonic oscillator, the specific configuration corresponding to the embodiment is appropriately employed or various improvements or modifications may be made.

(System Configuration)

Figure 1:
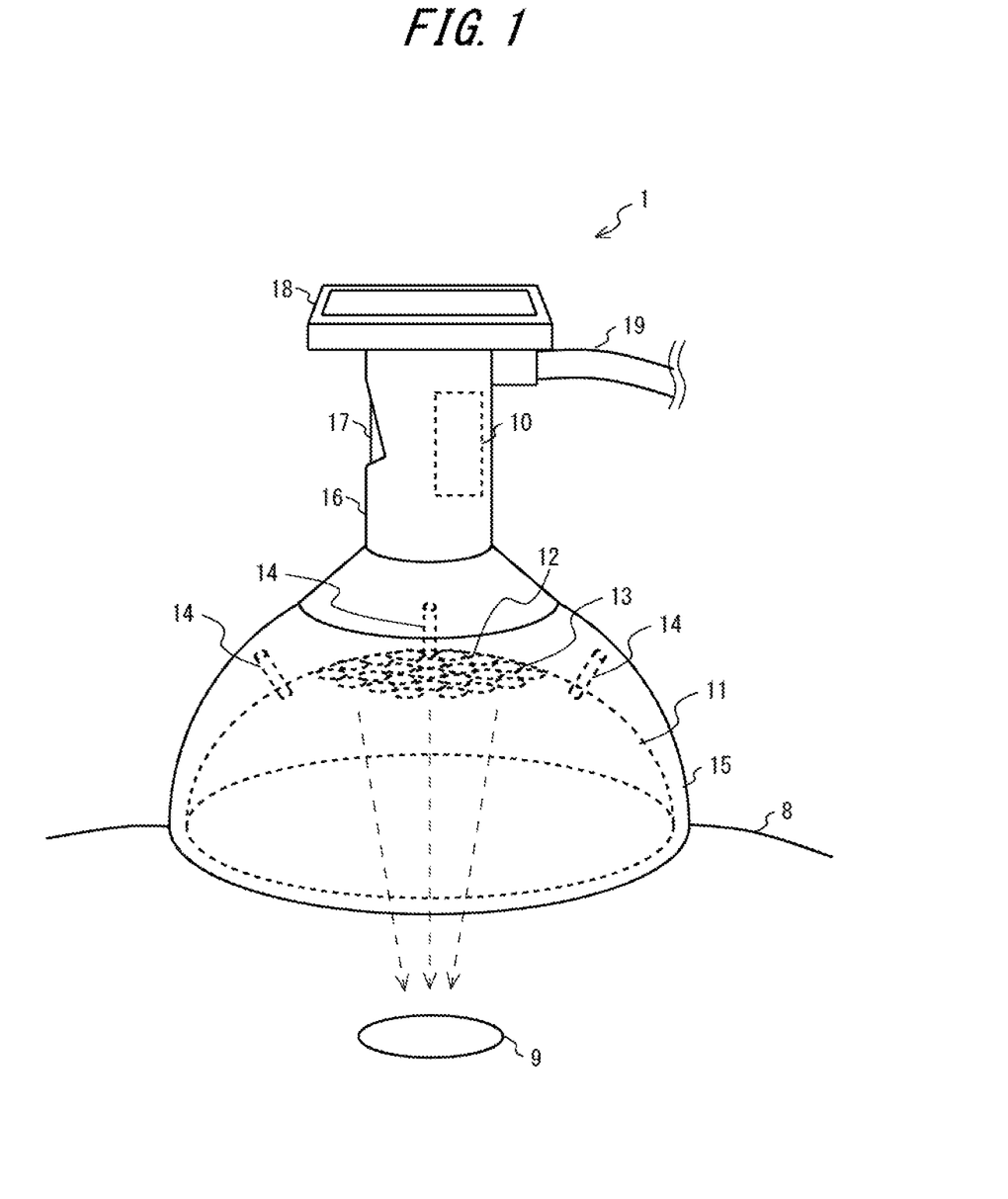
FIG. 1 is a view showing the outline of an ultrasonic oscillator according to an embodiment.

FIG. 1 is a view showing the outline of the ultrasonic oscillator according to the embodiment. The ultrasonic oscillator according to the embodiment aims to increase the efficiency of heat treatment for a target in a living body using ultrasonic waves and the status confirmation of the treatment to reduce a burden on a physician (user) and realize more accurate treatment than ever before.

The ultrasonic oscillator according to the embodiment has a membrane 11 having a substantially hemispherical shape, an ultrasonic array 13 constituted by a plurality of ultrasonic oscillation elements 12 provided on the membrane 11, an actuator 14 provided on the outer surface of the membrane 11, a housing 15 in which the membrane 11 or the like is provided, a handle 16 provided at the upper end of the housing 15 and handled by a user, a lever 17 by which the user is allowed to perform an operation while holding the handle 16, a controller 10 that controls the ultrasonic oscillation elements 12, the actuator 14, or the like, a display 18 that is provided at the upper end of the handle 16 and displays image data or the like output from the controller 10 thereon, and a cable 19 connected to an external device. The cable 19 may include a communication cable, a power cable, a water-cooling pipe used to cool the ultrasonic oscillation elements 12, or the like. However, it is possible to appropriately make the omission, replacement, and addition of the specific hardware configuration of the ultrasonic oscillator according to the embodiment. For example, the display may not be included in the configuration of the ultrasonic oscillator, and a display connected to an outside in a wired or wireless fashion may be used instead.

The user is allowed to hold the handle 16 and freely move the ultrasonic oscillator on the front surface of a living body 8 including a heating target 9. In addition, the user is allowed to instruct the controller 10 to heat the heating target 9 (oscillate ultrasonic waves from the ultrasonic oscillation elements 12) by operating the lever 17 based on the confirmation of a display content on the display 18 while holding the handle 16.

Figure 2:
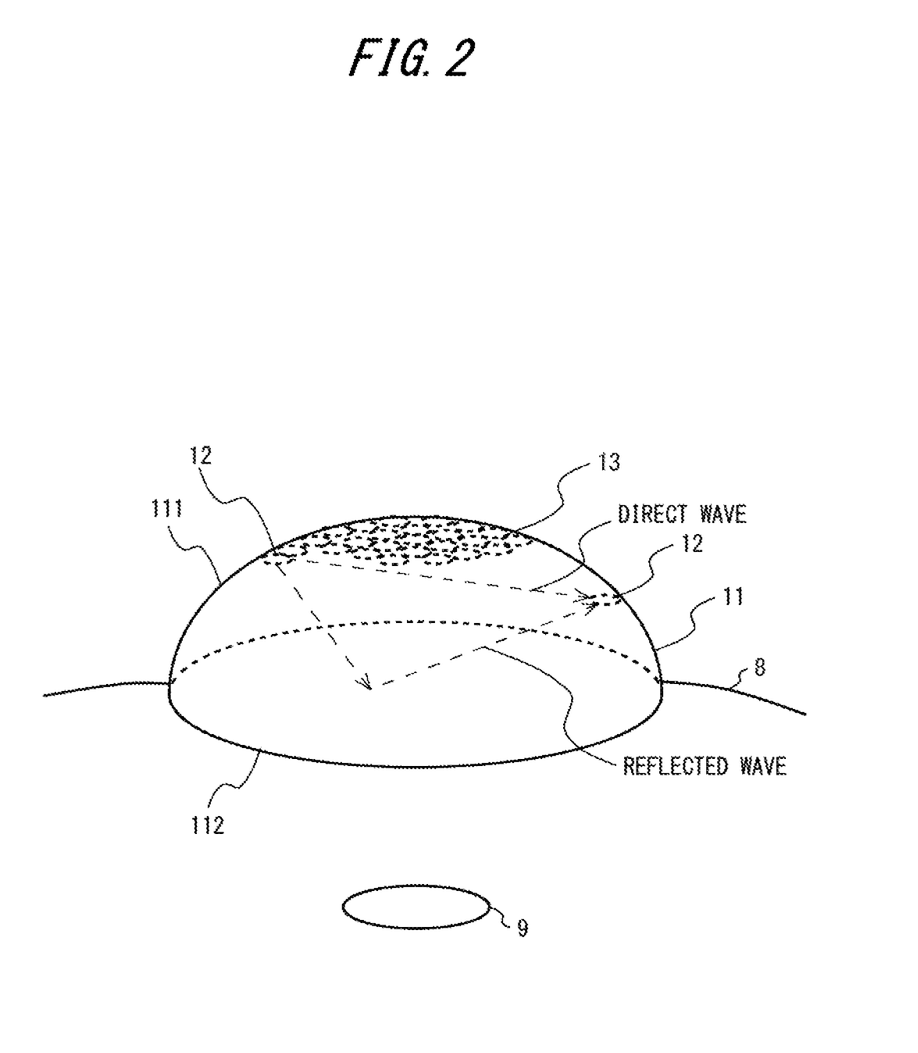
FIG. 2 is a cross-sectional view of the membrane of the ultrasonic oscillator according to the embodiment.

FIG. 2 is a cross-sectional view of the membrane 11 of the ultrasonic oscillator according to the embodiment. The membrane 11 is a member having a substantially hemispherical shape as a whole, the hemispherical shape having a concave portion 111 that forms a concave opposing the heating target 9 in a state in which the ultrasonic oscillator is directed to the heating target 9 and having a contact portion 112 that seals the opening of the concave portion 111 and contacts the living body 8 including the heating target 9. The concave portion 111 has the substantially hemispherical shape in the embodiment, but it may employ other shapes. For example, the concave portion 111 may employ a cone shape, a truncated cone shape, a half-turn ellipsoid shape, shapes approximating these shapes, or the like.

The outer shell of the membrane 11 is made of an elastic material, and the inside of the membrane 11 is filled with gel. Therefore, the concave portion 111 and the contact portion 112 of the membrane 11 are made deformable. Note that the inside of the membrane 11 may be filled with any substance so long as the substance is adaptable to the deformation of the concave portion 111 and may be filled with, for example, liquid. In addition, for the transmission of ultrasonic waves, the substance filling the membrane 11 and the inside of the membrane 11 is preferably a medium that does not greatly absorb the ultrasonic waves, realizes a transmission speed close to a speed at which the ultrasonic waves pass through a living body, and has uniformity hardly causing irregularities.

Moreover, the plurality of ultrasonic oscillation elements 12 is held side by side on the inner side surface of the concave portion 111 of the membrane 11. Thus, the plurality of ultrasonic oscillation elements 12 is arranged along the concave opposing the heating target 9 to constitute the ultrasonic array 13 having a concave shape. That is, in the embodiment, the membrane 11 also functions as a retention portion that retains the ultrasonic oscillation elements 12. However, the plurality of ultrasonic oscillation elements 12 may be retained on the outer side surface of the concave portion 111 of the membrane 11.

The actuator 14 (driver) is connected to the membrane 11 and deforms the concave portion 111 of the membrane 11 by driving. In the embodiment, a plurality of linear actuators 14 is provided so as to connect the membrane 11 and the housing 15 surrounding the membrane 11 to each other. When the respective linear actuators 14 implement drive according to an instruction from the controller 10, the concave portion 111 deforms. However, the configuration of the driver shown in the embodiment is just an example, and means for deforming the concave portion 111 with a driver is not limited to the example of the embodiment. For example, a mechanism similar to a mechanism for opening/closing an umbrella may be provided so as to surround the concave portion 111 of the membrane 11 and opened/closed with one actuator to deform the concave portion 111. In addition, the driver is allowed to deform the concave portion 111 even if it is not connected to the housing 15.

Moreover, in the embodiment, the plurality of ultrasonic oscillation elements is also used as sensing means (sensors) for sensing the direct waves or reflected waves of ultrasonic waves oscillated from other ultrasonic oscillation elements. When sensing the direct waves or reflected waves of the ultrasonic waves oscillated from other ultrasonic oscillation elements, the plurality of ultrasonic oscillation elements outputs sensing signals corresponding to the amplitudes, frequencies, phases, or the like of the sensed ultrasonic waves to the controller 10. After receiving the sensing signals, the controller 10 generates three-dimensional image data on a reflecting target including the heating target 9 using sensing signals based on reflected waves among the received sensing signals. In the embodiment, the ultrasonic oscillation elements are also used as the sensors for sensing. However, the sensors for sensing may be provided separately from the oscillation elements. In addition, oscillation and sensing for treatment and oscillation and sensing for imaging may be performed using the same ultrasonic array or may be performed using an ultrasonic array for treatment and an ultrasonic array for imaging that are separately provided. When the ultrasonic array for treatment and the ultrasonic array for imaging are separately provided, they may be laminated together on the concave portion 111 or may be dispersedly arranged on the same layer.

The controller 10 is a computer having a central processing unit (CPU), a random access memory (RAM), a read only memory (ROM), a storage (auxiliary memory), a communication interface, or the like (each of which is omitted in the figures). The controller 10 performs the following various control processing in such a way that the CPU runs a program read from the storage and developed into the RAM or a program stored in the ROM. However, it is possible to appropriately make the omission, replacement, and addition of the specific hardware configuration of the controller 10 according to the embodiment. In addition, the controller 10 is not limited to a single unit. The controller 10 may be realized by a plurality of units using the technology of so-called cloud computing or dispersed computing or the like.

The controller 10 controls the ultrasonic oscillation elements 12 so as to oscillate ultrasonic waves. More specifically, in a state in which the focal point of ultrasonic waves to be oscillated from the plurality of ultrasonic oscillation elements 12 is positioned at the heating target 9, the controller 10 controls the respective elements so as to oscillate the ultrasonic waves to heat the heating target 9. Here, the controller 10 controls the plurality of ultrasonic oscillation elements 12 so as to adjust the phases of the ultrasonic waves oscillated from the ultrasonic oscillation elements 12 to perform the control of a heating position of the ultrasonic waves, the cancellation of the heating, or the like. Note that as a specific method for changing a heating position (focal position) under phase control, it is possible to employ an ultrasonic phased array technology in which the phases of ultrasonic waves output from respective elements are made different to generate pseudo different oscillation points to control the direction of a combined wave. In the embodiment, the controller 10 controls the phases of the ultrasonic waves output from the respective elements so as to control the direction of a combined wave and adjust the heating position.

In addition, the controller 10 controls the actuator 14 so as to push/pull the concave portion 111 to be deformed and adjust the oscillation directions of the ultrasonic waves oscillated from the plurality of ultrasonic oscillation elements 12 to control the heating position (focal position) of the ultrasonic waves oscillated from the plurality of ultrasonic oscillation elements 12. As described above, the plurality of ultrasonic oscillation elements 12 that oscillates the ultrasonic waves is provided on the concave portion 111 of the membrane 11 to constitute the ultrasonic array 13. Therefore, when the concave portion 111 deforms by means of the actuators 14, the plurality of ultrasonic oscillation elements 12 moves correspondingly. As a result, the oscillation directions of the ultrasonic waves from the respective ultrasonic oscillation elements 12 change. The ultrasonic oscillator according to the embodiment deforms the concave portion 111 in the way described above, which makes it possible to adjust the oscillation directions of ultrasonic waves and a heating position.

(Operation Procedure)

Next, a description will be given of a procedure for treatment using the ultrasonic oscillator according to the embodiment. Note that the specific content, order, or the like of processing that will be described in the embodiment is just an example for the implementation of the ultrasonic oscillator. The specific content, order, or the like of the processing may be appropriately selected according to the embodiment.

Figure 3:
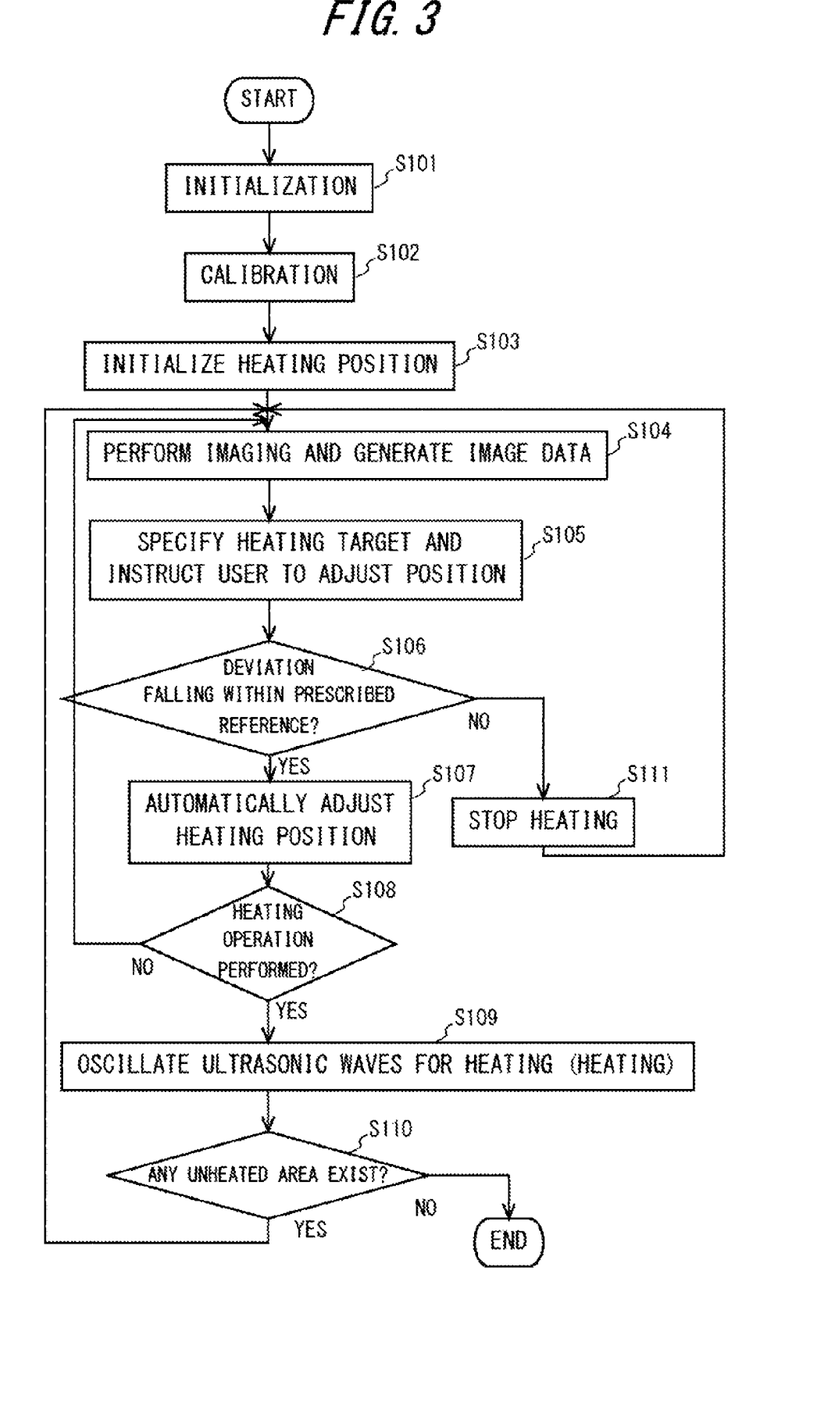
FIG. 3 is a flowchart showing the flow of heating processing in the embodiment.

FIG. 3 is a flowchart showing the flow of heating processing in the embodiment. The processing shown in the flowchart starts when power is input to the ultrasonic oscillator.

In step S101, initialization is performed. With the start of the ultrasonic oscillator, the controller 10 outputs a control signal prepared in advance for the initialization to the actuator 14 to control the same such that the curvature of the concave portion 111 of the membrane 11 becomes a prescribed initial value. After that, the processing proceeds to step S102.

In step S102, calibration is performed. The controller 10 applies driving voltage to a prescribed number of the ultrasonic oscillation elements 12 (hereinafter called "elements for imaging") among those in the ultrasonic array 13 to oscillate ultrasonic waves. The oscillated ultrasonic waves are sensed (received) as direct waves and reflected waves by other ultrasonic oscillation elements 12 not used in the oscillation. The elements having sensed the ultrasonic waves output sensing signals, and then the controller 10 having received the sensing signals acquire the amplitudes, frequencies, phases, or the like of the sensed ultrasonic waves from the sensing signals. In this way, the controller 10 is allowed to determine which ultrasonic oscillation elements 12 have oscillated the sensed ultrasonic waves. In addition, as for ultrasonic waves oscillated from the same ultrasonic oscillation elements 12 and then sensed, the controller 10 calculates time (hereinafter called "direct-wave transmission time") required when direct waves reach from the oscillation elements to sensing elements and calculates time (hereinafter called "reflected-wave transmission time") required when reflected waves reach from the oscillation elements to sensing elements. Then, based on the direct-wave transmission time and the reflected-wave transmission time calculated for the plurality of ultrasonic oscillation elements 12, the controller 10 calculates a reflection surface and the positions and oscillation directions (postures) of the respective ultrasonic oscillation elements 12. After that, the processing proceeds to step S103.

Note that the embodiment describes an example in which the calibration is performed every time the ultrasonic oscillator starts. However, the calibration performed in step S102 may be omitted. In case that the calibration is omitted, the controller 10 is allowed to use parameters set in advance as the positions and oscillation directions (postures) of the respective ultrasonic oscillation elements 12.

In step S103, the initialization of a heating position is performed. Based on the positions and directions of the respective ultrasonic oscillation elements 12 calculated in step S102, the controller 10 operates the actuator 14 to change the curvature of the concave portion 111 of the membrane 11. In addition, the controller 10 sets up the phases of ultrasonic waves for heating oscillated from the ultrasonic oscillation elements 12 to adjust a focal point (heating position) when the ultrasonic waves are oscillated by the ultrasonic array 13 to an initial position. Specifically, the controller 10 retains in advance a formula or a table in which the correspondence relationship between the curvature of the concave portion 111, the positions and directions of the ultrasonic oscillation elements 12, and the focal point (heating position) is defined. The controller 10 acquires a required curvature based on the positions and directions of the respective ultrasonic oscillation elements 12 calculated in step S102 and a position required to be set as the focal point (the front surface or the inside of the living body 8 including the heating target 9 in the embodiment). Moreover, the controller 10 also retains a formula or a table in which the correspondence relationship between the operation amounts (pushing/pulling amounts) of the respective actuators 14 and the curvature of the concave portion 111 is defined. The controller 10 acquires the operation amounts of the actuators 14 based on the acquired curvature to control the actuators 14. After that, the processing proceeds to step S104.

In step S104, imaging and the generation of image data are performed. The controller 10 applies voltage for oscillating ultrasonic waves for imaging to elements for imaging in the ultrasonic array 13 to perform the oscillation of ultrasonic waves toward the living body 8 and the reception of reflected waves, the generation of image data based on the reflected waves, and the storage processing of the image data accompanied by the oscillation of the ultrasonic waves. More specifically, the controller 10 amplifies and digitizes sensing signals output from elements having received reflected waves to generate three-dimensional image data inside the living body 8 including the heating target 9 based on the reflected waves. For the generation of three-dimensional image data using reflected waves, a related art used in an echographic investigation or the like may be employed. In addition, the controller 10 specifies a position in the three-dimensional image data corresponding to the coordinates of the heating position (focal position) based on the curvature of the current membrane 11, the setting of the phases of the ultrasonic waves for heating, or the like.

In step S105, the heating target 9 is specified and displayed. The controller 10 specifies the heating target 9 in the image and stores information on the position of the heating target 9 in the image together with the image data. In addition, the controller 10 generates two-dimensional image data based on the three-dimensional image data acquired in step S104 and further specifies the position of the heating target 9 and the heating position (focal position) in the two-dimensional image data. The heating position in the two-dimensional image data may be specified in such a way that the controller 10 projects the heating position in the three-dimensional image data acquired in step S104 onto the two-dimensional image data. Then, the controller 10 outputs the generated two-dimensional image data together with a display showing the position of the heating target 9 and the focal position in the two-dimensional image data and causes the same to be displayed on the display 18. After that, the processing proceeds to step S106.

Here, the specification of the heating target 9 in two-dimensional image data is performed based on an input by a user when the processing of step S105 is performed for the first time after the processing shown in the flowchart starts. When the processing of step S105 is performed for the second and subsequent times, the specification of the heating target 9 in two-dimensional image data is performed based on the comparison (matching) between image data acquired when the processing of step S105 is previously performed and image data acquired when the processing of step S105 is performed this time.

More specifically, when the processing of step S105 is performed for the first time, the controller 10 causes two-dimensional image data to be displayed on the display 18 and receives a designating operation by the user who has confirmed a displayed image to specify the position of the heating target 9 in the image data. Here, the designating operation by the user represents, for example, a touching operation in which the user touches the displayed position of the heating target 9 on the display when the display 18 is a touch-screen type display. The controller 10 stores the position of the heating target 9 in the image data designated by the user and the characteristics of the image. The embodiment employs as an example a mode in which the heating target 9 is specified based on the designation by the user. However, other techniques may be employed to specify the heating target 9. For example, it may be possible to employ a mode in which the heating target 9 is automatically specified by the controller 10 based on the brightness, tone, or the like of the respective pixels of image data.

When the processing of step S105 is performed for the second and subsequent times, the controller 10 compares (matches) image data newly generated by imaging in step 3104 with previous image data. Thus, the controller 10 determines which position of the newly-generated image data corresponds to the heating target 9 specified in the previous image data and specifies the position, which has been determined to be the position corresponding to the heating target 9 specified in the previous image data, as the heating target 9 in the newly-generated image data.

In addition, in step S105, the controller 10 compares the position of the heating target 9 with the heating position (focal position) in the image data and generates and outputs instructing information for guiding the heating position to the position of the heating target 9. More specifically, the controller 10 compares the heating target 9 with the heating position in the image data in a coordinate system to calculate the deviation between the focal position and the heating target 9. Then, when the deviation between the focal position and the heating target 9 exists, the controller 10 plots and outputs instructing information such as an arrow that connects the focal position in the image data and a prescribed position included in the area of the heating target 9 (for example, a gravity position in the area of the heating target 9) to each other, and then causes the same to be displayed on the display 18 so as be overlapped with an image based on the image data. The user sees the instructing information displayed on the display 18, determines a direction and a movement amount for moving the ultrasonic oscillator based on, for example, the direction, length, or the like of the arrow, and operates the handle 16 to move the ultrasonic oscillator such that the concave of the membrane 11 is set at an appropriate position and has an appropriate angle. After that, the processing proceeds to step S106.

In step S106, a determination is made as to whether the deviation between the heating position and the heating target 9 falls within a prescribed reference. The controller 10 compares the position of the heating target 9 with the heating position (focal position) in the image data to determine whether the deviation between the position of the heating target 9 and the heating position exceeds the prescribed reference. Here, the prescribed reference represents the upper limit of a range within which the deviation calculated in step S105 is correctable by the change of the curvature of the concave portion 111 of the membrane 11 according to the control of the actuators 14 and correctable by the control of the phases of the ultrasonic waves oscillated from the ultrasonic oscillation elements 12. When it is determined that the deviation exceeds the prescribed reference, the processing proceeds to step S111. On the other hand, when it is determined that the deviation falls within the prescribed reference, the processing proceeds to step 3107.

In step S107, the heating position is adjusted. When it is determined in step S106 that the deviation between the position of the heating target 9 and the heating position falls within the prescribed reference, the controller 10 adjusts the heating position (focal position) according to the latest information (image data, an analysis result, the position of the heating target 9) acquired by the imaging such that the focal point (the heating position) of the ultrasonic waves oscillated by the ultrasonic array 13 is set on the near side or the back side of the heating target 9. Here, the adjustment of the heating position is performed by the change of the curvature of the concave portion 111 of the membrane 11 according to the control of the actuators 14 and/or performed by the control of the phases of the ultrasonic waves oscillated from the ultrasonic oscillation elements 12. For the adjustment, a specific method for controlling the actuators 14 is roughly the same as the method described in step S103.

In addition, in step S107, the controller 10 may control the plurality of ultrasonic oscillation elements 12 to adjust the phases of the ultrasonic waves oscillated from the respective ultrasonic oscillation elements to cancel some of the ultrasonic waves oscillated in step S109 that will be described later such that an area to be heated by the ultrasonic waves is limited. More specifically, when the heating target specified in step S105 is smaller in size than a heating area about a focal point, the controller 10 causes some of the ultrasonic oscillation elements to oscillate ultrasonic waves having a phase opposite to that of ultrasonic waves oscillated from other ultrasonic oscillation elements in an area to which heating is not desirably applied. When the controller 10 performs the phase control as described above, the ultrasonic waves cancel each other in the area to which heating is not desirably applied to cancel the heating. That is, the ultrasonic oscillator according to the embodiment cancels heating in some area even if a heating target is smaller in size than a heating area about a focal point, which makes it possible to prevent areas other than the heating target from being heated while heating the heating target. After that, the processing proceeds to step S108.

In step S108, a determination is made as to whether the user has given a heating instruction. While the processing shown in the flowchart is performed, the user confirms the image displayed on the display 18. When determining from the displayed image that the heating target may be heated, the user operates the lever 17 to instruct the controller 10 to heat the heating target 9 (oscillate the ultrasonic waves from the ultrasonic oscillation elements 12). When the user operates the lever 17, the heating instruction is given to the controller 10. The controller 10 determines whether the heating instruction has been given from the user through the lever operation. When it is determined that the heating instruction has not been given, the processing returns to step S104. On the other hand, when it is determined that the heating instruction has been given, the processing proceeds to step S109.

In step S109, the oscillation of ultrasonic waves for heating is performed. The controller 10 having been given the heating instruction causes the ultrasonic oscillation elements 12 to oscillate the ultrasonic waves for heating while successively moving the heating position (focal position) in the area of the heating target 9 from the near side or the back side of the heating target 9 to heat the heating target 9. Note that on this occasion, the controller 10 accumulates the areas of the heating target 9 to which the heating has been applied (heated areas). After that, the processing proceeds to step S110.

In step S110, a determination is made as to whether any unheated area exists. The controller 10 compares the entire area of the heating target 9 in the retained image data with the heated areas accumulated in the processing of step S109 to determine whether any unheated area exists in the heating target 9. When it is determined that no unheated area exists (the heating target 9 has been entirely heated), the processing shown in the flowchart ends. On the other hand, when it is determined that any unheated area exists, the processing proceeds to step S104.

Note that the processing from step S104 to step S110 shown in the flowchart is repeatedly performed on a regular basis (for example, every 0.1 second) for the second and subsequent times. Thus, the ultrasonic oscillator according to the embodiment is allowed to heat the heating target 9 while easily adjusting the heating position to an appropriate position.

In step S111, the heating is stopped. When it is determined in step S106 that the deviation between the position of the heating target 9 and the heating position exceeds the prescribed reference, the controller 10 causes an alert to be displayed on the display 18 and stops the oscillation of the ultrasonic waves from the plurality of ultrasonic oscillation elements 12. Note that in the embodiment, the controller 10 stops the supply of power to the ultrasonic oscillation elements 12 to stop the oscillation. After that, the processing returns to step S104.

That is, according to the processing shown in the flowchart, the heating automatically resumes when the user operates the handle 16 while operating the lever to adjust the heating position so as to fall within the area of the heating target 9 (or fall within an automatically adjustable area in step S107). However, when the heating position is not corrected into an appropriate position even if prescribed time (for example, a few seconds) elapses, the processing shown in the flowchart may automatically end regardless of the lever operation by the user.

The ultrasonic oscillator according to the embodiment does not require means for moving and controlling the ultrasonic oscillation elements 12 with high accuracy unlike devices in the related art and replaces a user's manually adjustment operation with the change of the curvature of the membrane 11 and the phase control. Thus, the ultrasonic oscillator is allowed to exactly and easily heat the heating target 9.

What is claimed is:

1. An ultrasonic oscillator comprising:
    a plurality of ultrasonic oscillation elements configured to emit ultrasonic waves;
    a retention portion including a deformable and substantially hemispherically-shaped concave portion having a concave surface configured to oppose a heating target, the plurality of ultrasonic oscillation elements being arranged on the concave surface and forming a first focal spot, a curvature of the concave surface of the deformable concave portion being changed by elastic deformation of the concave portion, and positions of the plurality of ultrasonic oscillation elements retained on the concave surface of the concave portion being changed by the change to the curvature of the concave surface by the elastic deformation of the concave portion to have a second focal spot for a heating position in the heating target;
    a driver that is connected to the retention portion and configured to elastically deform the concave portion to change the curvature of the concave portion; and
    a controller configured to control the ultrasonic oscillation elements to emit the ultrasonic waves and to control the heating position of the emitted ultrasonic waves by controlling the driver to deform the concave portion to change the curvature of the concave surface of the concave portion and adjust propagation directions of the emitted ultrasonic waves to have the second focal spot for the heating position.

2. The ultrasonic oscillator according to claim 1, wherein the retention portion is a hollow member partially having the concave portion.

3. The ultrasonic oscillator according to claim 2, further comprising:
    one of liquid and gel filling the hollow of the retention portion.

4. The ultrasonic oscillator according to claim 2, wherein the heating target is included in a living body, and
    the retention portion has a contact portion configured to contact the living body and seal an opening of the concave portion.

5. The ultrasonic oscillator according to claim 1, wherein the controller controls the plurality of ultrasonic oscillation elements so as to adjust phases of the ultrasonic waves oscillated from the plurality of ultrasonic oscillation elements, thereby controlling the heating position of the ultrasonic waves oscillated from the plurality of ultrasonic oscillation elements.

6. The ultrasonic oscillator according to claim 5, wherein the controller controls the phases of the ultrasonic waves oscillated from the plurality of ultrasonic oscillation elements such that the ultrasonic waves oscillated from the plurality of ultrasonic oscillation elements cancel each other in a partial area, thereby cancelling the heating in the partial area.

7. The ultrasonic oscillator according to claim 1, further comprising:
    sensors that sense the ultrasonic waves emitted from any of the plurality of ultrasonic oscillation elements, wherein
    the controller receives sensing signals output from the sensors.

8. The ultrasonic oscillator according to claim 7, wherein the sensors are arranged along the concave surface of the concave portion of the retention portion.

9. The ultrasonic oscillator according to claim 7, wherein the controller generates and outputs image data on a reflecting target including the heating target using sensing signals based on reflected waves among the received sensing signals.

10. The ultrasonic oscillator according to claim 9, further comprising a display that displays the output image data thereon.

11. The ultrasonic oscillator according to claim 9, wherein the controller compares a position of the heating target with the heating position in the image data and generates and outputs instructing information for guiding the heating position to the position of the heating target.

12. The ultrasonic oscillator according to claim 9, wherein the controller compares the position of the heating target with the heating position in the image data and stops the emission of the ultrasonic waves by the plurality of ultrasonic oscillation elements when a deviation between a position of the heating target and the heating position exceeds a prescribed reference value.

13. An ultrasonic oscillator comprising:
    a plurality of ultrasonic oscillation elements that are configured to emit ultrasonic waves and to sense the emitted ultrasonic waves;
    a retention portion including a deformable and substantially hemispherically-shaped concave portion having a concave surface configured to oppose a heating target, the plurality of ultrasonic oscillation elements being arranged on the concave surface and forming a first focal spot, a curvature of the concave surface of the deformable concave portion being changed by elastic deformation of the concave portion, and positions of the plurality of ultrasonic oscillation elements retained on the concave surface of the concave portion being changed by the change to the curvature of the concave surface by the elastic deformation of the concave portion to have a second focal spot for a heating position in the heating target;

a driver that is connected to the retention portion and configured to elastically deform the concave portion to change the curvature of the concave portion; and a controller configured to control the ultrasonic oscillation elements to emit the ultrasonic waves and to receive sensing signals output from the ultrasonic oscillation elements and to control the heating position of the emitted ultrasonic waves by controlling the driver to deform the concave portion to change the curvature of the concave surface of the concave portion and adjust propagation directions of the emitted ultrasonic waves to have the second focal spot for the heating position.

* * * * *